United States Patent
Kovacs

(10) Patent No.: US 12,350,115 B2
(45) Date of Patent: Jul. 8, 2025

(54) CLAMP WITH MOUNT FOR A SURGICAL RETRACTOR

(71) Applicant: INNOVATIVE MEDICAL PRODUCTS, INC., Plainville, CT (US)

(72) Inventor: Tamas Kovacs, Burlington, CT (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 11 days.

(21) Appl. No.: 18/301,489

(22) Filed: Apr. 17, 2023

(65) Prior Publication Data

US 2024/0341912 A1 Oct. 17, 2024

(51) Int. Cl.
*A61B 90/57* (2016.01)
*A61B 17/02* (2006.01)

(52) U.S. Cl.
CPC .......... *A61B 90/57* (2016.02); *A61B 17/0206* (2013.01)

(58) Field of Classification Search
CPC ................ A61B 90/57; A61B 17/0206; A61B 2090/571; A61G 13/0063
See application file for complete search history.

(56) References Cited

U.S. PATENT DOCUMENTS

| | | | |
|---|---|---|---|
| 5,000,163 A | | 3/1991 | Ray et al. |
| 5,462,551 A | * | 10/1995 | Bailey .................... A61B 90/50 606/88 |
| 5,535,973 A | | 7/1996 | Bailey et al. |
| 7,380,299 B1 | | 6/2008 | Demayo |
| 8,683,630 B2 | | 4/2014 | Rolfes |
| 9,615,987 B2 | * | 4/2017 | Worm .................. A61G 13/129 |
| 10,004,569 B2 | | 6/2018 | Singh et al. |
| 2015/0250672 A1 | | 9/2015 | Fossez et al. |
| 2016/0287237 A1 | * | 10/2016 | Demayo ................ A61B 50/15 |

FOREIGN PATENT DOCUMENTS

DE 102015121734 A1 6/2017

* cited by examiner

*Primary Examiner* — Si Ming Ku
(74) *Attorney, Agent, or Firm* — Wasserbauer Law LLC; Nicholas E. Blanton, Esq.; Damian G. Wasserbauer, Esq.

(57) ABSTRACT

A clamp with mount for a surgical retractor is disclosed that is adapted to couple one or more surgical retractors to a base plate. The clamp is configured to allow the surgeon to secure, adjust, and/or remove the retractor system with one hand, and without the need for an assistant to perform such manipulation. The clamp for a base plate also holding the body portion of the patient advantageously reduces the complexity and disadvantages of conventional surgical retractor systems by locating the mount for a surgical retractor below the surgical site in a manner that keeps the body portion and OR table as free as possible from associated obstruction by the retractor system.

3 Claims, 6 Drawing Sheets

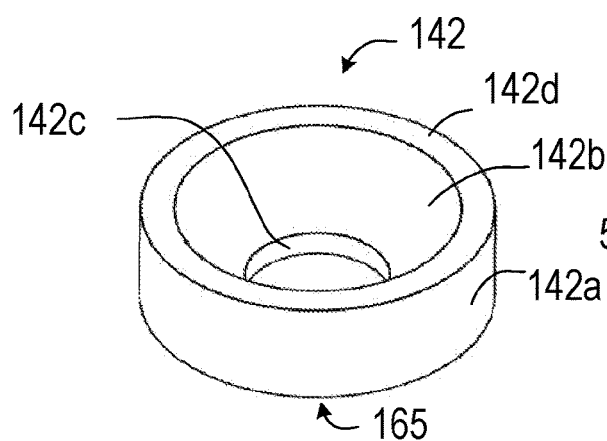
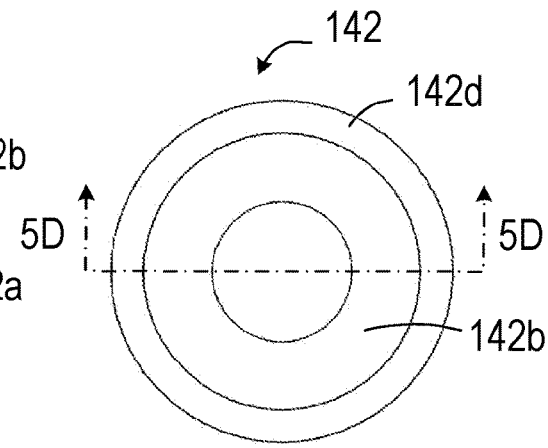
FIG. 5A  FIG. 5B
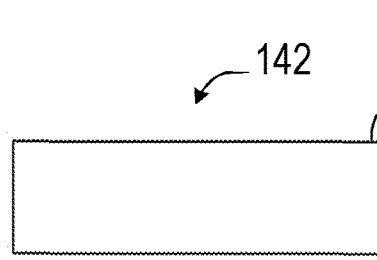
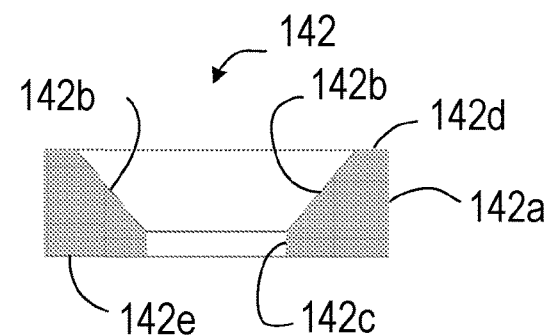
FIG. 5C  FIG. 5D

CLAMP WITH MOUNT FOR A SURGICAL RETRACTOR

TECHNICAL FIELD

The present invention relates to retractor systems for use during surgical procedures in general, and in particular to clamps adapted to mount a surgical retractor to a base plate.

BACKGROUND

During surgical procedures, a surgeon typically makes an incision in a body part of a patient to access a localized internal area for a particular surgical procedure and a surgical retractor system is used to maintain holding the patient's soft tissue away from the surgical site in a suitable manner providing clear access to the localized internal area. Conventional surgical retractor systems typically have a rail clamp for clamping to the side rail of an operating table, a joint clamp for clamping a rod to the rail clamp, one or more additional joint clamps used for clamping one or more retractor blades to the rod, and/or elastic bands that provide a certain degree of tension to aid in holding the patient's soft tissue away from the surgical site.

Conventionally, an assistant is needed to help the surgeon assemble, adjust, and/or remove the surgical retractor system. Because the conventional systems use side rail clamp (s) to form the base attachment point for a surgical retractor system, such as the side rail on the opposite side of the OR table from the side where the surgeon is located, a surgical assistant is typically needed to aid the surgeon with assembling, adjusting, and/or removing the side rail clamp and adjacent components. Moreover, conventional side rail clamps do not provide for single-handed adjustment. Consequently, use of surgical retractor systems is not practical without the help of an assistant. Furthermore, the presence of an assistant whose purpose it is to adjust the surgical retractor system during the surgery interferes insofar as having an additional person observing and/or being gathered around a relatively small surgical site. These disadvantages are particularly applicable in partial or total knee replacement surgeries.

Accordingly, what is needed is a base clamping mount for a surgical retractor system that overcomes these disadvantages of the conventional approaches while maintaining or improving the stability and positioning of the patient.

SUMMARY

It is an object of the present invention to provide a clamp with a mount for a surgical retractor system that is slidably adjustable along the track of a base plate without angular deflection of the body of the clamp relative to the track.

It is another object of the present invention to provide a clamp with a mount for a surgical retractor system that is positioned under, and proximate the medial or lateral side, of the knee replacement surgical site, thereby reducing the distance from the one or more mounts to the one or more retractors for optimal positioning of the system.

It is another object of the present invention to provide a clamp with a mount for a surgical retractor system that can easily be assembled, adjusted, and/or removed by the surgeon and/or via a single hand.

It is another object of the present invention to provide a clamp with a mount for a surgical retractor system that can be easily disassembled and sterilized.

It is another object of the present invention to provide increased stability and positioning of the limb of the patient.

Other desirable features and characteristics will become apparent from the subsequent detailed description, the drawings, and the appended claims, when considered in view of this summary.

DESCRIPTION OF THE DRAWINGS

Non-limiting and non-exhaustive embodiments of the present disclosure are described with reference to the following drawings. In the drawings, like numerals describe like components throughout the several views.

For a better understanding of the present disclosure, reference will be made to the following Detailed Description, which is to be read in association with the accompanying drawings, which are incorporated in and constitute a part of this specification, show certain aspects of the subject matter disclosed herein and, together with the description, help explain some of the principles associated with the disclosed implementations, wherein:

FIG. 5A illustrates a perspective view of a coupling, according to an embodiment of the present invention;

FIG. 5B illustrates a top view of a coupling thereof;

FIG. 5C illustrates a front view of a coupling thereof;

FIG. 5D illustrates a cross-sectional view of a coupling, taken along the line shown in FIG. 5B thereof.

DETAILED DESCRIPTION

Figure 1A:
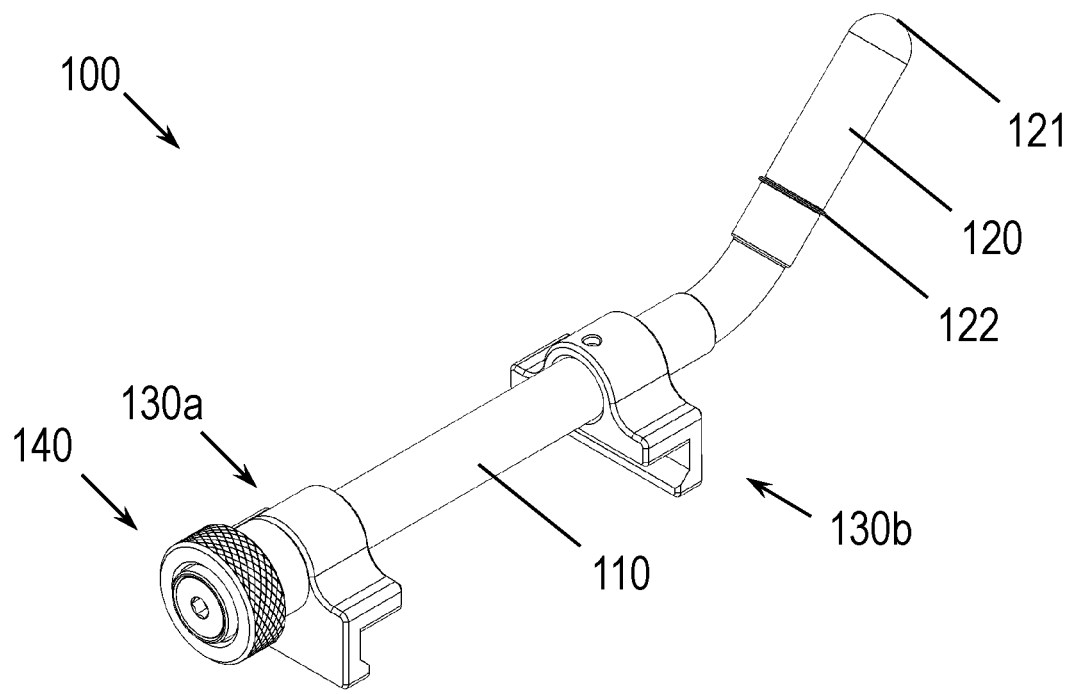
FIG. 1A illustrates a front, top, right-side perspective view of a clamp with a mount for a surgical retractor system, according to an embodiment of the present invention.

Non-limiting embodiments of the invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention. The drawings featured in the figures are provided for the purpose of illustrating some embodiments of the invention and are not to be considered as a limitation thereto.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive. Also, the term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

Figure 1B:
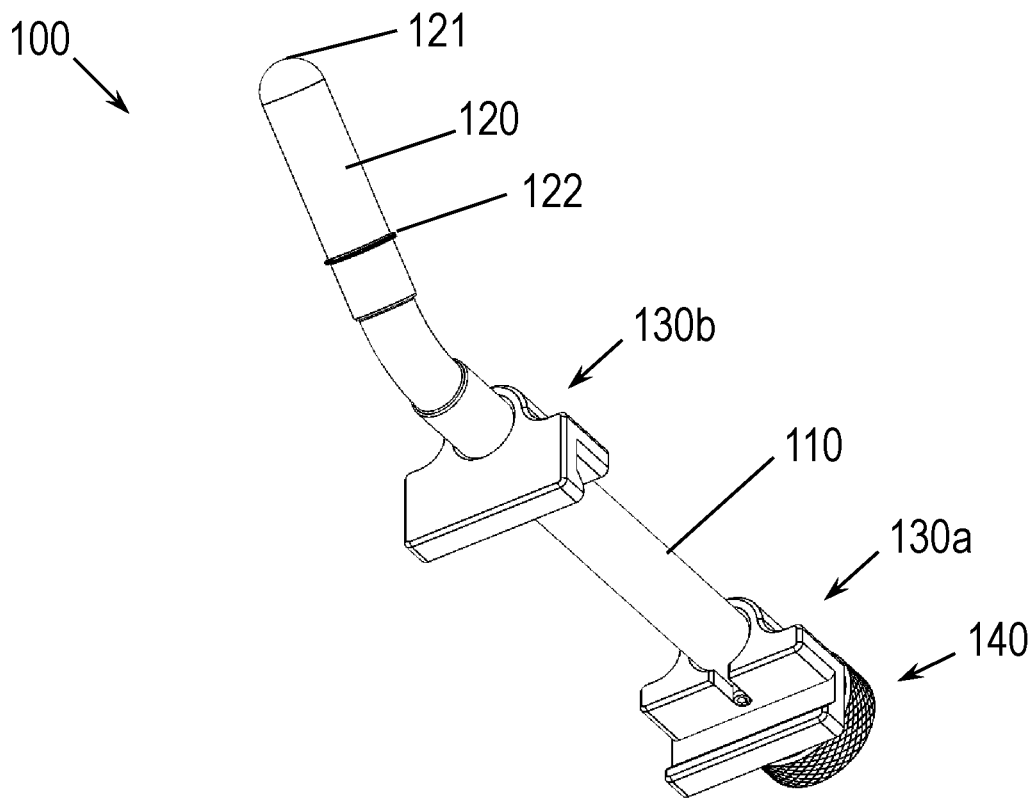
FIG. 1B illustrates a rear, bottom, left-side perspective view of a clamp with a mount for a surgical retractor system thereof.
Figure 6:
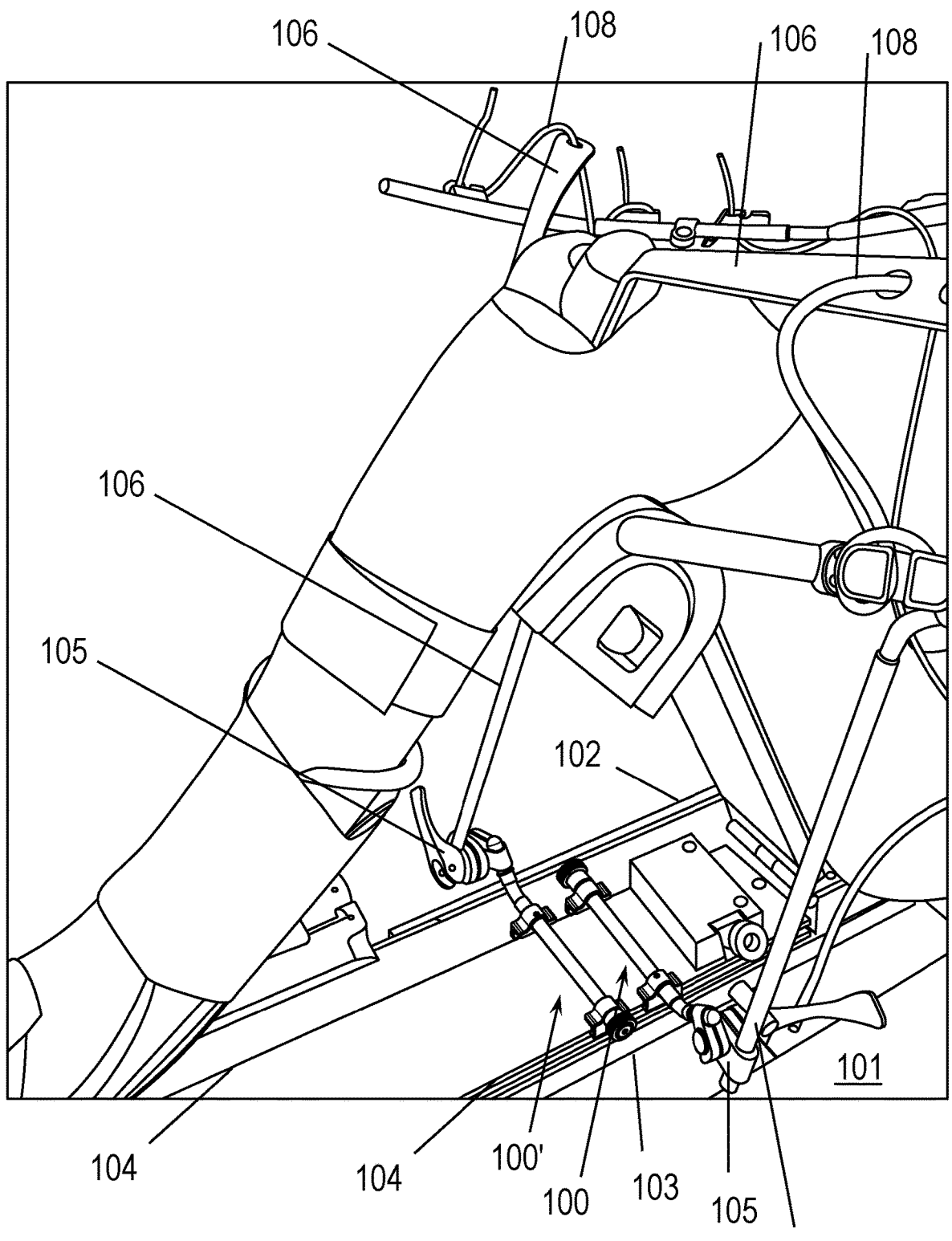
FIG. 6 illustrates an environmental view of a clamp with a mount for a surgical retractor system in the environment of a knee replacement surgery, according to an embodiment of the present invention.

Referring to FIGS. 1A and 1B, and 6, a clamp 100 with mount for a surgical retractor is generally designated as element 100. The clamp 100 is configured to be secured by operably coupling to a track portion 104 of a base plate 103 that is set upon a surgical support table or operating table 102. The base plate 103 may be any suitable base plate for surgical applications, such as a base plate product manufactured and offered for sale by In Innovative Medical Products, Inc. as the De Mayo Adapt2Fit® Modular Knee Positioner, which is also shown and described in Pat. Pub. No. US-2022-0273512-A1, which is incorporated herein by reference in its entirety.

Figure 2:
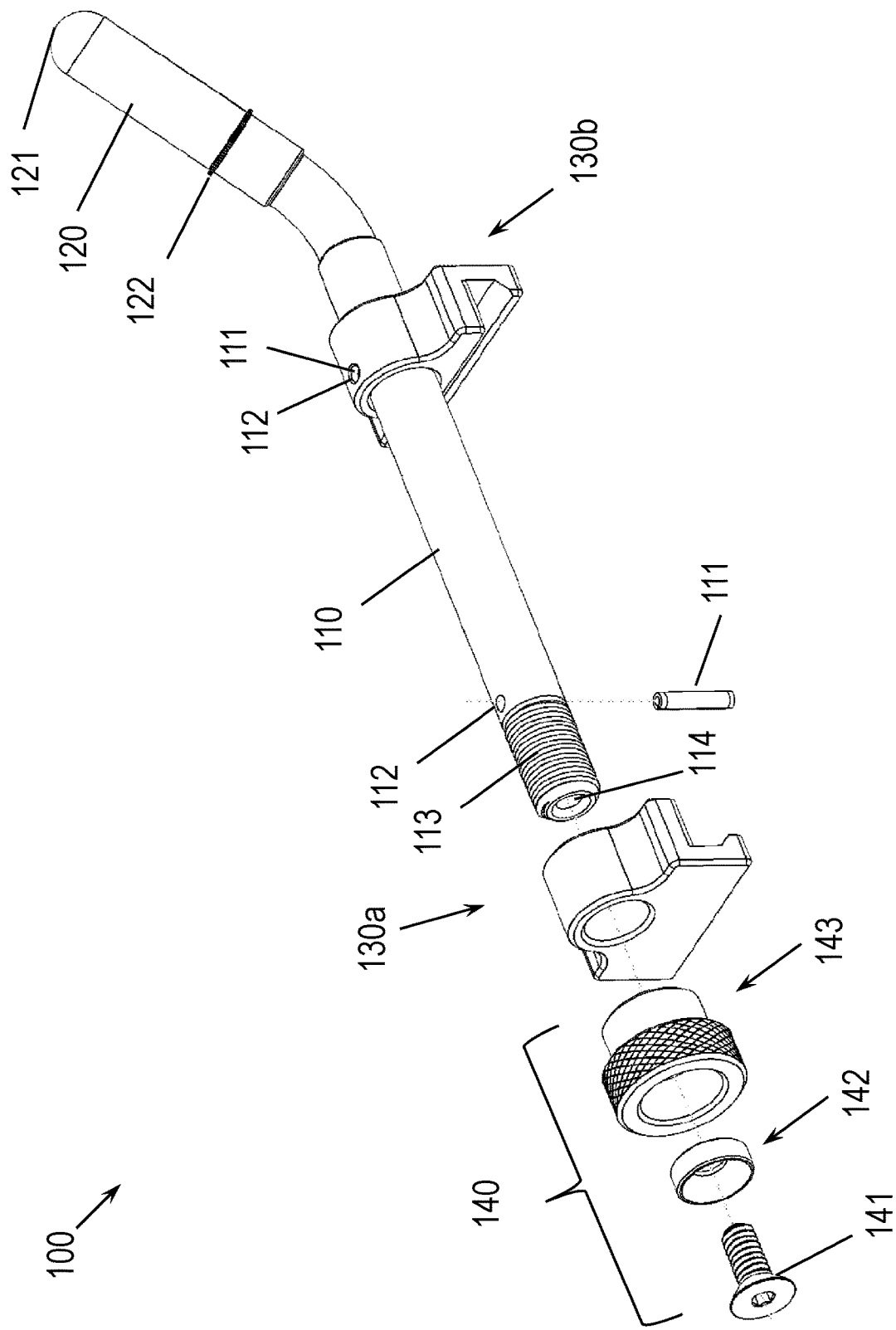
FIG. 2 illustrates an exploded, front, top, right-side perspective view of a clamp with a mount for a surgical retractor system thereof.

As shown in FIGS. 1A-6, the clamp 100 has a body 110 having a mount portion 120, at least one track arm 130, and a fastener assembly 140. In a preferred embodiment, the clamp 100 comprises first and second track arms 130a, 130b, respectively, wherein the first track arm 130a is adapted for linear translation along body 110 to provide a clamping action, and the second track arm 130b is rigidly affixed to body 110, such as through welding, adhesive, press fitting, affixed with a set screw, or other know method of affixing. For example, a pin opening 112 formed continuously through the second track arm 130b and the body 110 may be configured to accept a pin 111, such as a slotted spring pin, as shown in FIG. 2. Alternatively, the second track arm 130b may be formed integrally with the body 110. Mount portion 120 may include mount end 121 and a mount flange 122. The body 110, pin 111, first track arm 130a, second track arm 130b, and fastener assembly 140 are adapted for disassembling with ease for sterilization and storage. Preferably, the clamp 100 is made of metal, such as stainless steel. Alternatively, any suitable material may be used having sufficient strength and sterilization properties.

In operation, the mount portion 120 is sized and/or otherwise adapted to accept a joint clamp 105 of a retractor system, whereby the mount end 121 may be rounded or tapered to help fit joint clamp 105 thereto, and the mount flange 122 prohibits further movement of the joint clamp 105 along the body 110. The size and orientation of the mount portion 120 provides critical advantages. For example, mount portion 120 may be disposed at an angle θ, as in FIG. 4B, which is generally purposed to allow access to mount portion 120 up and away from components lying therebelow, while also being distanced or otherwise positioned, so that the mount portion 120 and surgical retractor system coupled thereto remain offset from the patient limb, thereby allowing for unobstructed full compression and/or unobstructed full extension and positions of the limb therebetween. In a preferred embodiment this angle θ=45 degrees. Alternatively, the angle may be disposed 30 degrees≤θ≤60 degrees. Alternatively, the angle may be disposed 15 degrees≤θ≤75 degrees. In other embodiments, the mount portion 120 angle θ may be adjustable, such as via a set of interlocking teeth and fastener or other method known to one skilled in the art.

Figure 3A:
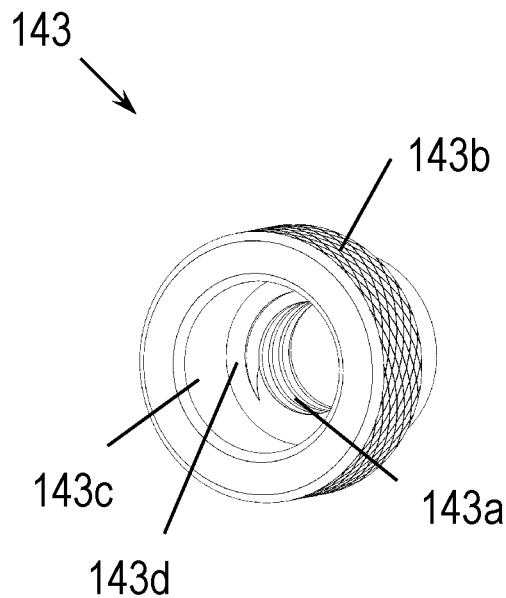
FIG. 3A illustrates a perspective view of a clamp fastener, according to an embodiment of the present invention.

Referring to the exploded view of FIG. 2, at an end opposite mount portion 120, the body 110 may have an attachment portion 113 such as body outer threaded portion 113 and body inner threaded portion 114. Fastener assembly 140 may be generally purposed to operably couple to body 110 along at least a portion of attachment portion 113 to move first track arm 130a toward or away from second track arm 130b to perform a clamping action. In the preferred embodiment, fastener assembly 140 may include a fastener 141, a coupling 142, and a clamp fastener 143. The fastener 141 may be a threaded fastener such as a hex screw 141, bolt, or any other fastener suitable to securely couple the coupling 142 to the body 110. The coupling 142, as illustrated in FIGS. 5A-5D, may include a cylindrical outer surface 142a, a tapered inner surface 142b, a cylindrical inner surface 142c, a top 142d, and a bottom 142e. Clamp fastener 143, as illustrated in FIG. 3A, may include a clamp fastener threaded portion 143a, a knob portion 143b, a recess portion 143c, and an abutment portion 143d. Knob portion 143b may be formed as a knurled knob to facilitate gripping by the hand of a surgeon and ensure a good grip for advancing or retracting the clamp fastener 143 as desired for operating with a single hand. In an assembled configuration, as in FIGS. 1A-1B, 4A-4B, and 6, a fastener 141 couples to coupling 142 along a tapered inner surface 142b, the head of fastener 141 being formed of a complementary shape as that of the tapered inner surface 142b. Then the threads of fastener 141 are fully threaded into body inner threaded portion 114 of body 110 until a portion of the bottom 142e abuts the end of body 110, thereby forming a locking mechanism thereby securing and inhibiting the clamp fastener 143 from being removed from the clamp 100. In this manner, when assembled, the clamp fastener 143 may move along body 110 via the threaded engagement of the body outer threaded portion 113 and the clamp fastener threaded portion 143a. In turn, the clamp fastener 143 may operably engage the first track arm 130a moving the same toward or away from the second track arm 130b to provide clamping to the base plate 103.

Figure 3B:
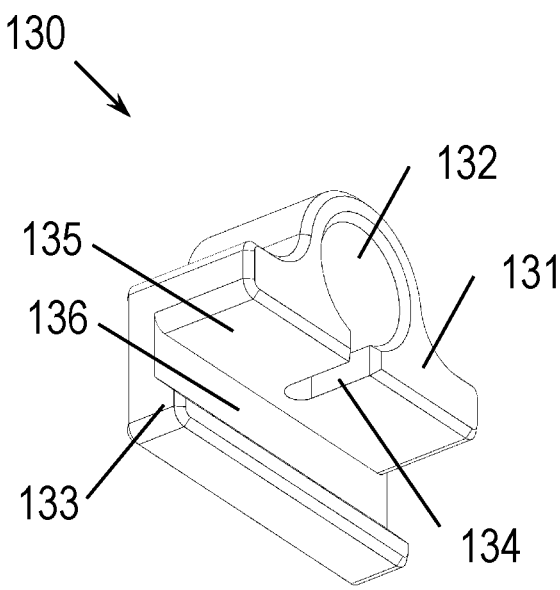
FIG. 3B illustrates a perspective view of a track arm, according to an embodiment of the present invention.
Figure 3C:
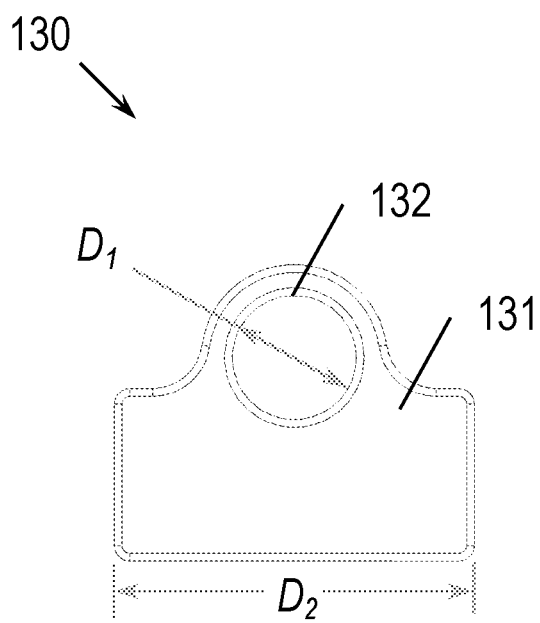
FIG. 3C illustrates a front view of a track arm thereof.
Figure 3D:
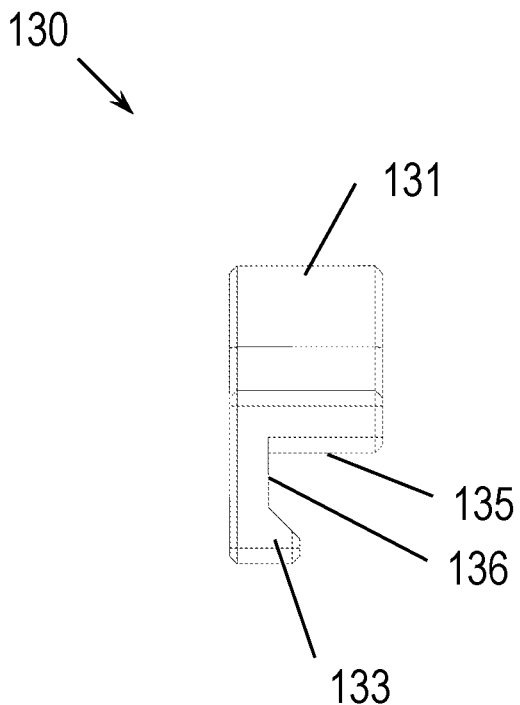
FIG. 3D illustrates a side view of a track arm thereof.

Referring to FIGS. 3B-3D, the track arm 130, such as a first track arm 130a or a second track arm 130b is described. Track arm 130 comprises a track arm body 131, a body receiver 132, a track flange 133, a pin slot 134, a top track surface 135, and a side track surface 136. The body receiver 132 may be sized appropriately within manufacturing tolerances to receive the body 110 portion and to allow translation therealong but not angular displacement. The track flange 133, top track surface 135, and side track surface 136 operate to engage the track portion 104 of the base plate 103 when the clamp fastener 143 is tightened so as to secure and hold the clamp 100 against the track 104, as illustrated in FIGS. 4B and 6. Pin slot 134 is adapted to inhibit rotational movement of the track arm 130 about the body 110 so that movement of track arm 130a is limited to a single degree-of-freedom, i.e., linear translation.

Referring to FIG. 6, one or more clamps 100 according to the invention are shown in use, where a surgical retractor system has been assembled and a knee surgery has commenced. The one or more clamps 100 may be disposed on the base plate 103 via secured coupling to track portion 104 by tightening of the clamp fastener 143. In FIG. 6, one clamp 100 is disposed having the mount portion 120 positioned on the medial side, and another clamp 100' having the mount portion 120 positioned on the lateral side. One side of a joint clamp 105 may be coupled to the mount portion 120 of clamp 100. The other side of the joint clamp 105 may then be coupled to a rod 106. Rod 106 may then extend upwardly towards the knee, and one or more retractors 108 may then hold soft tissue of the patient in a desired position, where the retractor 108 is being held in a tensioned position via one or more elastic bands 108 coupling the retractor 108 to the rod 106. Advantageously, the mount portion 120 positions the surgical retractor system components directly to either side of the patient's limb in a manner that reduces parts and reduces the distance that the system is mounted relative to the surgical site, as compared to conventional options that utilize direct coupling of the surgical retractor system to a side rail 102 of the OR table 101. Furthermore, the clamp 100 is accessible by the surgeon directly, for assembling, repositioning during the surgery, and/or removal of the surgical retractor system, such as may be desirable when the leg is fully compressed, i.e., heel against buttocks, or fully extended.

The clamp 100 according to the present invention also limits movement of the clamp 100 to a linear translation along the track 104, which aids the surgeon or robotic device during surgery by allowing for accurate and incremental change of positioning of the surgical retractor system. For example, in a preferred embodiment, a second dimension $D_2$ of the track arm 130 can be about three times (3×) that of a first dimension $D_1$. First dimension $D_1$ may correspond to the diameter of the rod 106 and/or body 110, where the rod 106 and body 110 are roughly equivalent for acceptance into joint clamp 105. Because the second dimension $D_2$ is at least about three times the first dimension $D_1$, the clamp 100 is advantageously adapted to prohibit angular translation of the clamp 100 and/or body 110 relative to the track 104 of base plate 103 and/or operating table 101. In this context, "about" refers to +/−10 This prohibits the retractor structure, including the joint clamp 105, rod 106, and retractor 107 from folding, collapsing, or otherwise repositioning in an undesirable manner when the surgeon loosens, but does not fully remove clamp 100 for slidably adjusting the same along track 104.

Figure 4A:
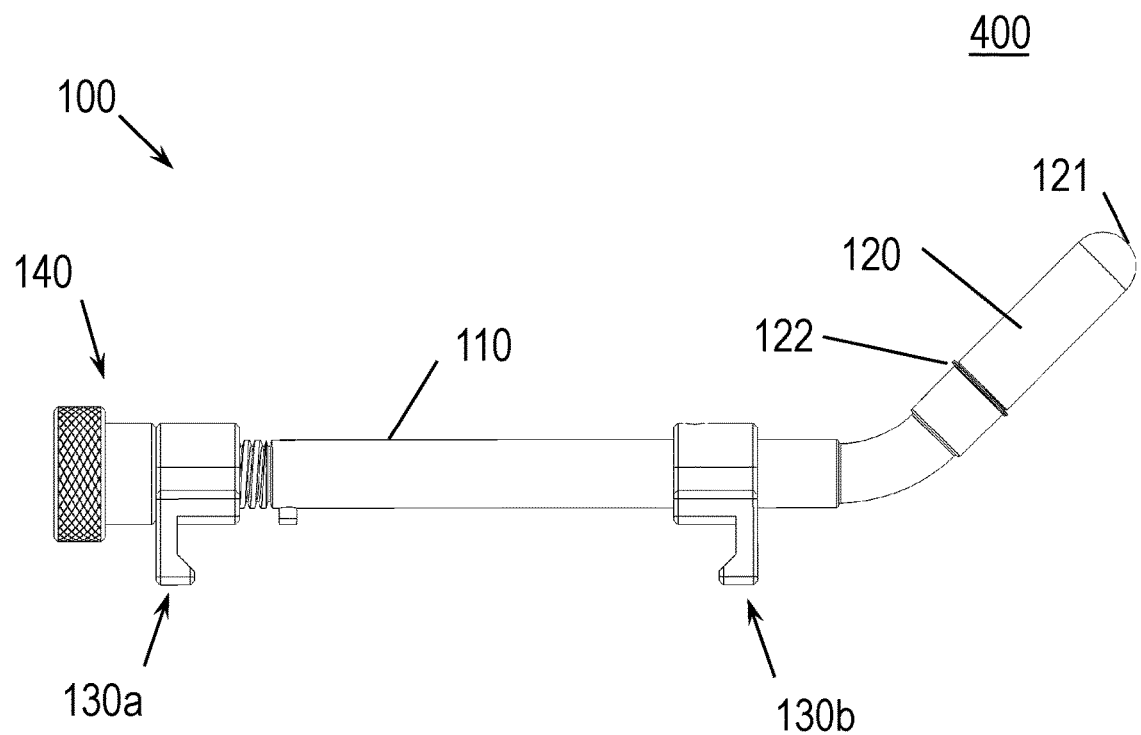
FIG. 4A illustrates a right-side view of a clamp with a mount for a surgical retractor system in an open position, according to an embodiment of the present invention.
Figure 4B:
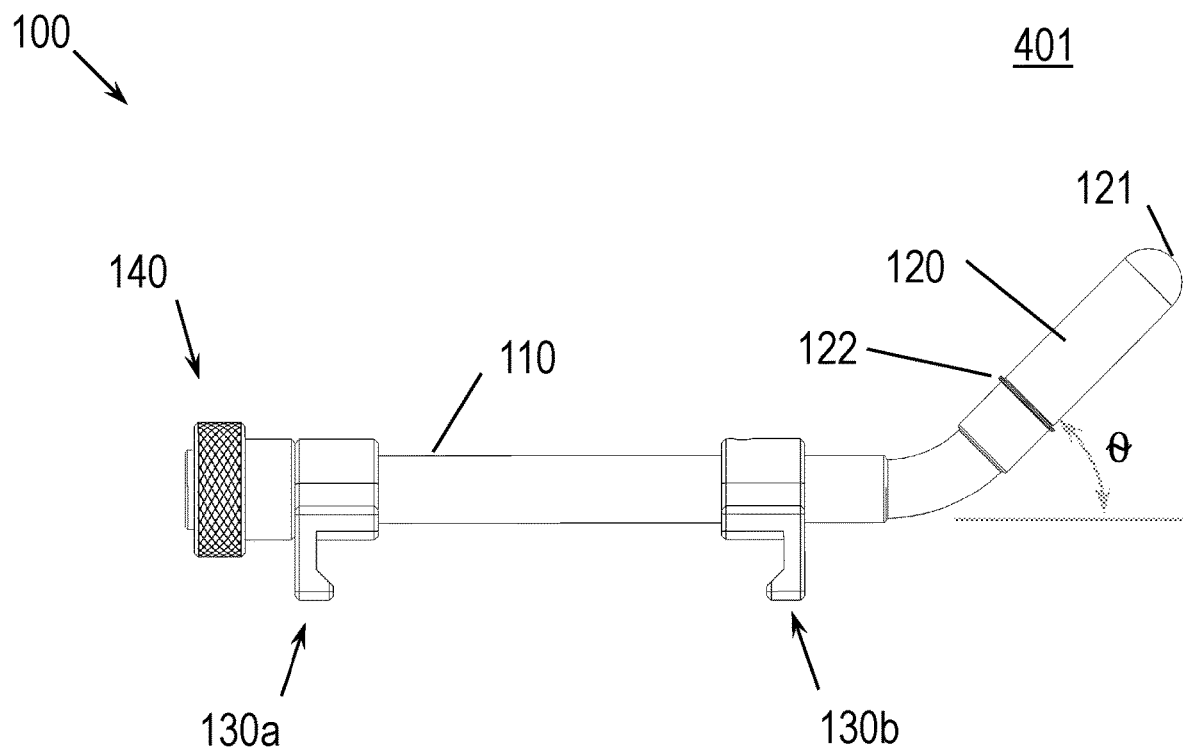
FIG. 4B illustrates a right-side view of a clamp with a mount for a surgical retractor system in a closed position, according to an embodiment of the present invention.

To assemble clamp 100 on the track 104 of base plate 103, the surgeon or other personnel may first manipulate clamp fastener 143 and track arm 130a to a first portion 400, as illustrated in FIG. 4A. The clamp 100 may then be positioned appropriately over the track 104. Then, the clamp 100 may be moved to a second position 401 by tightening of the fastener assembly 140, as shown in FIG. 4B. Because pin 111 disposed in pin opening 112 proximate first track arm 130a prohibits rotation of track arm 130a, this facilitates the clamp 100 in producing only a linear translation when the clamp is slightly loosened. For example, the clamp 100 may be adapted to provide about two full rotations of clamp fastener 143 to move clamp 100 from the first position 400 to the second position 401. Then, a loosening for slidably translating clamp 100 along track 104 may be achieved by about a, for example, quarter counter-clockwise turn of clamp fastener 143 from second position 401.

The previous description of the disclosed embodiments is provided to enable any person skilled in the art to make or use the invention. Various modifications to these embodiments will be readily apparent to those skilled in the art, and the principles defined herein can be applied to other embodiments without departing from the spirit or scope of the invention. It is therefore desired that the present embodiments be considered in all respects as illustrative and not restrictive, reference being made to the appended claims as well as the foregoing descriptions to indicate the scope of the invention.

What is claimed is:

1. A clamp for coupling to a track portion of a base plate for knee replacement surgery, the clamp comprising:
   a body including a pin disposed outwardly therefrom;
   a mount portion disposed at an end of said body, said mount portion adapted to couple to a surgical retractor system;
   a fastener assembly disposed at another end of said body;
   a first track arm disposed proximate, and further inward relative to, said fastener assembly; and
   a second track arm disposed proximate, and further inward relative to, said mount portion;
   said first and second track arms each respectively comprising:
      a track arm body including a body receiver for receiving said body, said body receiver having a dimension $D_1$,
      a track flange, a top track surface, and a side track surface, each extending between a first side and a second side, said first and second sides offset by a dimension $D_2$, wherein $D_2$ is about three times that of $D_1$, said track flange, said top track surface and said side track surface adapted to receive said track portion for slidable linear translation and/or positioning of said clamp therealong,
   said first track arm further comprising a pin slot adapted to receive said pin of said body for prohibiting rotation of said first track arm about said body,
   said fastener assembly adapted to move said first track arm from a first position to a second position, said first position characterized by said clamp being removeable from said track portion, said second position characterized by said clamp being fixedly coupled to said track portion, and
   an intermediate position characterized as being between said first position and said second position such that said clamp is adapted to linearly translate along said track portion of said base plate.

2. The clamp of claim 1, wherein said another end comprises a body outer threaded portion and a body inner threaded portion.

3. The clamp of claim 2, wherein said fastener assembly further comprises:
   a fastener to rigidly couple a coupling by threaded engagement of said body inner threaded portion; and
   a clamp fastener including a clamp fastener threaded portion for threaded engagement of said body outer threaded portion, said coupling adapted to hold said clamp fastener to said body when said clamp is in said first position.

* * * * *